United States Patent [19]

Calanchi et al.

[11] Patent Number: 5,008,117

[45] Date of Patent: Apr. 16, 1991

[54] FORMULATION FOR PREPARING EXTEMPORANEOUS HOMOGENEOUS MICROCAPSULE SUSPENSION

[75] Inventors: Massimo Calanchi, Monza; Leonardo Gentilini, Milano; Marco Marconi, Cinisello Balsamo, all of Italy

[73] Assignee: Eurand Italia SPA, Milano, Italy

[21] Appl. No.: 287,401

[22] Filed: Dec. 20, 1988

Related U.S. Application Data

[63] Continuation-in-part of Ser. No. 2,660, Nov. 26, 1986, abandoned.

[30] Foreign Application Priority Data

May 8, 1985 [IT] Italy ............................. 20617 A/85
May 2, 1986 [EP] European Pat. Off. .......... 8600280

[51] Int. Cl.$^5$ ..................... A61K 9/16; A61K 9/50; A61K 9/62; B01J 13/02
[52] U.S. Cl. .................. 424/494; 252/315.3; 252/363.5; 424/452; 424/461; 424/490; 424/493; 424/496; 424/497; 428/402.24; 514/952; 514/974
[58] Field of Search ............... 252/315.3, 363.5; 428/402.24; 424/452, 461, 490, 494; 514/974, 952

[56] References Cited

U.S. PATENT DOCUMENTS

| | | | |
|---|---|---|---|
| 3,872,227 | 3/1975 | Hoff et al. | 514/198 |
| 4,126,672 | 11/1978 | Sheth et al. | 424/452 |
| 4,155,741 | 5/1979 | Scher et al. | 424/419 X |
| 4,189,499 | 2/1980 | Tosi et al. | 514/555 |
| 4,460,563 | 7/1984 | Calanchi | 424/498 X |

FOREIGN PATENT DOCUMENTS 844772 8/1960 United Kingdom .

*Primary Examiner*—Richard D. Lovering
*Attorney, Agent, or Firm*—Gordon W. Hueschen

[57] ABSTRACT

The invention relates to a method by which it is possible to prepare a formulation consisting of thickening or suspending agents and other excipients, having the property of dispersing and dissolving quickly in water or aqueous vehicles, without clot formation, with which it is possible to prepare an extermoraneous homogeneous suspension of solid particles and more particularly of micro-encapsulated drugs, which otherwise have the tendency to precipitate or float.

22 Claims, No Drawings

FORMULATION FOR PREPARING EXTEMPORANEOUS HOMOGENEOUS MICROCAPSULE SUSPENSION

The present application is a continuation-in-part of our prior-filed copending application, Ser. No. 002,660, filed Nov. 26, 1986, now abandoned.

The present invention relates to a process for obtaining a pharmaceutical formulation, adapted to administer microcapsules of a drug in the form of a single dose bag, contents of which are poured in water at the moment of use.

In the description and claims the terms have the following meanings:

"microcapsule" is used to indicate particles of drugs, powders, crystals, granules, pellets and also liquid droplets, coated with a polymeric membrane.

"microencapsulation" is generally the process used for applying the membrane.

"single dose bag" is a bag-like container for a single dose of active substance and the formulation excipients.

"thickening or suspending agents" are water-soluble substances varying density and viscosity so as to allow suspension of solid particles.

Microencapsulation is a well-known process consisting in coating substances with a continuous film on the basis of natural or synthetic polymers.

There are several microencapsulation methods, and many of them and the corresponding patents are cited and described in the works "Microcapsules and Microencapsulation Techniques" (published in the year 1976) and "Microcapsules and other Capsules. Advance since 1975" (published in the year 1979), both by M. H. Gutcho. Among the preferred methods, those disclosed in U.S. Pat. Nos. 3,196,827 and 3,253,944 to D. E. Wurster should be mentioned, relating to mechanical coating methods consisting in spraying the membrane around particles by means of suitable equipment, and those disclosed in U.S. Pat. Nos. 3,415,758, 3,155,590 and 3,341,416, relating to chemical-physical coating methods based on coacervation or phase separation, where the membrane-forming polymer is dissolved in a suitable solvent or microencapsulation vehicle and the substance to be dissolved is suspended in such a solution and kept under agitation. Coacervation of the polymer around the substance to be coated is obtained in several ways, for instance by temperature variation, addition of another polymer which is more soluble in the vehicle, addition of a non-solvent for the membrane-forming polymer, and so on. The membrane may be hardened and then microcapsules are separated from the vehicle, e.g., by filtration or centrifugation, and finally dried.

In the pharmaceutical field microencapsulation is used to obtain masking of unpleasant taste, to delay drug release, to prevent irritation by contact of drugs with the gastrointestinal mucous membrane, to protect drugs from ambient decay, to separate drugs which are reactive to each other, and to transform the drug into a form that can be used more readily, such as conversion from liquid condition into a powder comprised of microcapsules.

For administering microencapsulated drugs there are several dosage forms, such as capsules, tablets and also single dose bags which are particularly suitable for preparing formulations of granules and powders and therefore of microcapsules. This is also the most suitable or even the sole existing approach in case of administration of microcapsules for high dosage drugs.

Single dose bags containing microcapsules were already prepared in the past, sometimes even on an industrial scale, as mentioned in the manual "Microencapsulation" by J. R. Nixon, Chapter 7, page 93, but they have several drawbacks particularly due to hydrorepellency of polymers forming the microcapsule membrane, such as polymers based on cellulosic or wax-like substances, and to specfic gravity of microencapsulated substances and therefore of said microcapsules. As a matter of fact, when the bag contents are poured as usual into water, milk, or fruit juices, microcapsules precipitate to the glass bottom or float on the liquid surface, sticking to the glass wall because of their hydrorepellancy. This causes a considerable inaccuracy in the drug dosage in addition to a poor compliance of the patient, who can see floating particles or has a scraping feeling in the mouth and throat when swallowing the final content of the glass, with its mass of precipitated particles.

The addition to the formulation of thickening agents might have delayed or even eliminated microcapsule separation, but has been found to give particularly negative results, because in contact with water these substances form clots which are dissolved slowly only under a vigorous mechanical agitation. An attempt was made to disperse these thickening substances together with the other formulation components by blending them in the conventional powder mixers but, even with such a strenuous measure, clot formation could not be prevented, but only partially reduced.

In order to solve these problems, Applicant effected thorough aimed experimental research so as to develop and perfect formulations for single dose bags which do not show the above-mentioned drawbacks and which make possible the use of microcapsules in such a dosage form.

Thus it was found that it is possible to attain this object by mixing, with the microcapsules, granules in which the thickening agent is suitably dispersed by a particular process which is the subject matter of the present invention.

As already stated, microcapsules may be prepared by several systems. To be suitable for this purpose, it is also necessary that the drug-coating membrane consist of a polymer approved for pharmaceutical use. Microcapsules usually consist of 3 to 50% by weight of polymer and 50 to 97% by weight of drug. The membrane-forming polymer should be permeable or soluble in the gastro-intestinal juices so as to allow drug release and absorption.

The preferred polymer used is ethylcellulose, but as non-limiting illustrative examples other polymers may also be cited, such as polyacrylates and polymethacrylates, polyvinylchloride, polyvinyl alcohol, polyethylene, polyamides, polysiloxanes, cellulose acetophthalate, hydroxypropylmethylcellulose phthalate, and also polymers of natural origin such as gelatin and gum arabic.

As to the drugs contained in the microcapsules, any pharmacologically-active substance, in liquid powdered, crystalline, or granular form, may be coated with a polymeric membrane by using a suitable microencapsulation method. As non-limiting examples are hereby cited: potassium chloride, theophylline, aminophylline, acetylsalicylic acid, paracetamol, lithium sulphate, ibuprofen, cimetidine, dextromethorphan HBr, phenylpropanolamine HCl, noscapine HCl, phenylephrine HCl, sodium dicloxacylline, sodium floxloxacilline, bacampicilline, methoclopramide, pseudoephedrine and organic and inorganic magnesium salts.

The process which is the subject matter of the present invention is now disclosed. It allows one to disperse the thickening substance among other components of the single dose bag, and preferably but not exclusively on the sweetening agents, in such a way that when the contents of the single dose bags are poured into water or other aqueous medium, a rapid dissolution of the thickening agent is obtained, which will not only eliminate clot formation, but will also give to the medium a viscosity sufficient to keep microcapsules in a homogeneous suspension for a period of several minutes, even some tens of minutes, so as to avoid the above-mentioned drawbacks, including separation of microcapsules and assumption of wrong dosages.

Said process substantially consists of the following steps:

(1) micronize, grind, or employ a thickening agent with a grain size less than 100 mesh and preferably less than 200 mesh (Tyler);

(2) suspend this fine powder of thickening agent in a solution containing a binder; the thickening agent must be insoluble or scarcely soluble in the solvent in which the binding agent is dissolved; this binder in its turn, besides being obviously soluble in the solvent, must also be water soluble, so as to bind the particles of thickening agent to the support described hereinbelow, but also to release them quickly once in contact with water;

(3) knead the suspension of step (2) with the granules or crystals of one or more other components of the formulation to be filled into the single dose bag.

In a wet granulation kneader or mixer, such as a planetary kneader, a rotary pan, a counterrotating horizontal blade mixer, a vertical centrifugal batch mixer, or the like, crystals or granules of one of the formulation components are placed. To this end the sweetener or other water-soluble excipient are preferably used, but mixtures of several components may also be used. The thickener suspension is then slowly poured into the kneader in one or more stages. Contents are then mixed so as to obtain a homogeneous distribution of the suspension around the granules or crystals of the solid excipient or excipients.

(4) The product so obtained is dried in an oven or fluidized bed.

The solvent evaporates and the thickener particles will remain stuck and homogeneously dispersed around the granules or crystals of solid excipient. The product obtained is finally sifted.

As thickening substances that may be used, the following non-limiting illustrative examples may be cited: alginates, carrageenan, agar-agar, tragacanth gum, xanthan gum, guar gum, locust bean gum, karaya gum, modified starch (e.g., corn starch), carboxymethylcellulose, microcrystalline cellulose (AVICEL RC-591 TM of FMC Corporation), alone or in combination with other hydrocolloids.

As binders which are soluble both in water and solvents, the following illustrative and non-limiting examples are cited: methylcellulose, hydroxypropylmethylcellulose, hydroxybutylmethylcellulose, hydroxyethylcellulose, hydroxypropylcellulose polyethyleneglycols, polyvinyl alcohols, polyvinylpyrrolidone.

As inert excipients which are commonly part of the composition of single dose bags, and on which the thickener coating suspension may be applied, the following illustrative and non-limiting examples are cited; sucrose, lactose, levulose, mannitol, dry sorbitol, maltodextrines, glycocoll, alanine, and pentaerythrite.

In order to facilitate dissolution of the suspending agent, a surfactant may be added to the formulation, such as dioctyl sodium sulphosuccinate, sodium laurylsulphate, a sorbitol or sorbitan ester with a fatty acid and so forth, which in some cases accelerates dissolution in water of the suspending agent since its wettability is made easier.

The surfactant may be added in any stage of the process, even if it is preferable to add it in the stage (2) of the above-described process, suspending it together with the thickening agent, or to mix it with the other excipients which are filled in the single dose bag.

The bags may be made with several materials, but the preferred one is aluminium foil laminated with a heat-weldable plastic film as it gives better waterproofing results.

The single dose bags are filled by a suitable apparatus using a loading tower, in which the mixture of drug microcapsules and the product prepared with the above process and of the other excipients required for the final formulation, such as flavouring and dyeing agents, are placed. However, for a better dosage precision, equipment with two loading towers is preferably used, from which the drug microcapsules and the granulate proposed with the foregoing process, blended with other possible formulation excipients, are separately filled into the bags.

The following examples of application should be construed as merely illustrative of the process of the present invention, but without any intention to limit the object and the scope of the invention.

EXAMPLE 1

(A) Preparation of microcapsules

Into a two-liter beaker, 1000 g of cyclohexane were placed. Under agitation 20 g ethylcellulose, 15 g polyethylene and 100 g potassium chloride crystals were added. The polymers were dissolved by heating to 78° C. Coacervation of ethylcellulose was obtained by cooling and ethylcellulose was deposited around the crystals of potassium chloride. Microcapsules were separated by filtration and dried in an oven with forced air circulation.

(B) Preparation of the suspending granulate 25 g Xanthan gum, having a grain size less than 200 mesh (Tyler), were suspended in 77.2 g of 3% solution of hydroxypropylcellulose in ethyl alcohol.

In a horizontal blade mixer 492 g of sucrose crystals were placed.

The suspension of Xanthan gum was slowly added in 15 minutes and the mixer was kept going for a further 30 minutes. The product was dried in an oven with forced air circulation and sifted with an 850 micron sieve.

(C) Preparation of single dose bags

The suspending granulate (B) was mixed for 10 minutes in a cube mixer with 7.5 g citric acid and 7.5 g orange flavouring. 5.140 g of this mixture and 0.860 g of potassium chloride microcapsules, equivalent to 10 mEq potassium, were filled in each single dose bag.

EXAMPLE 2

(A) Microcapsules were prepared with the same process disclosed in Example 1.

(B) following the process disclosed in Example 1, 850 g of granulate, containing Xanthan gum as thickener, were prepared.

(C) Granulate (B) was mixed in a cube mixer for 15 minutes with 150 g of anhydrous citric acid and 150 g of an orange flavouring different from that used in Example 1. Bags were then prepared using 10.5 of this mixture and 3.5 g of potassium chloride microcapsules, equivalent to 40 mEq of potassium.

EXAMPLE 3

(A) Microcapsules were prepared with the same process disclosed in Example 1.

(B) Same process and components of Example 1.

(C) 850 g of suspending granulate (A) were mixed in a cube mixer for 15 minutes with 50 g of citric acid and 150 g of orange flavouring of the same type used in Example 2. Bags were then prepared using 8.5 g of this mixture, that is a quantity less than Example 2, and 3.5 g of potassium chloride microcapsules equivalent to 40 mEq of potassium.

EXAMPLE 4

Bags prepared in the preceding examples differ from each other by the quantity of thickening agent and of microcapsules and therefore by the potassium dosage. Tests were effected to check that a homogeneous suspension is obtained, after having poured into water and stirred for one minute the contents of each bag, and that this suspension is stable for about two hours. The details and remarks are shown in the table.

| Example N° | Bag Weight | K Dose mEq | Water ml | Agitation sec | Suspension stability |||| 
|---|---|---|---|---|---|---|---|---|
| | | | | | 15 min | 30 min | 60 min | 120 min |
| 1 | 6 | 10 | 50 | 60 | good | good | good | sufficient |
| 2 | 14 | 40 | 200 | 60 | good | good | good | sufficient |
| 3 | 12 | 40 | 200 | 60 | good | good | good | suficient |

EXAMPLE 5

From the suspension prepared in Example 4, samples were taken at different times in order to find analytically the amount of potassium release from the microcapsules. The values found are reported in the following table, in which there are also given the details of the release analysis of the same KCl microcapsules, placed alone in the same conditions of the bags, as well as of the KCl microcapsules analyzed with the rotating blade method described in U.S.P., XXI Edition, page 1244.

| Example N° | Condition | % microcapsule release ||||
|---|---|---|---|---|---|
| | | 15 min. | 30 min. | 60 min. | 120 min. |
| 1 | 10 mEq/50 cc | 0.024 | 0.24 | 0.67 | 1.36 |
| 2 | 40 mEq/200 cc | 0.13 | 1.88 | 4.75 | 10.2 |
| 3 | 40 mEq/200 cc | 0.15 | 1.95 | 5.0 | 11.1 |
| only KCl | as Example 1 | 0.076 | 0.23 | 0.86 | 2.47 |
| microcapsules | as Ex. 2 and 3 | 0.55 | 1.87 | 5.0 | 10.9 |
| | USP | | 10.1 | 22.0 | 43.2 |

EXAMPLE 6

(A) The bitter taste of ibuprofen was masked by the following microencapsulation process: in a beaker with agitator 20 g gelatine, 20 g gum arabic and 1160 g of deionized water were added and heated up to 50° C. so as to obtain a solution in which 400 g of ibuprofen crystals with a grain size less than 500 microns were suspended. Solution pH was brought to a value between 4 and 6 and then slowly cooled to 15° C. The membrane deposited in this stage around the ibuprofen crystals was hardened with 10 g of 25% glutaric aldehyde in water. Three washings of microcapsules with deionized water were effected by stopping agitation and separating liquid from microcapsules by decantation. Microcapsules were filtered and dried in a fluidized bed by adding 20 g of highly-dispersed silica to make drying easier. The obtained microcapsules were sifted through a 600 micron sieve.

(B) The suspending granulate was prepared as described in Example 1.

(C) 520 g of granulate (B) were mixed for 15 minutes in a cube mixer with 7.5 g of citric acid and 7.5 g of orange flavouring. The single dose bags so prepared each contain 5.530 g of this mixture and 0.470 g of ibuprofen microcapsules equivalent to a dosage of 400 mg of active substance. When the bag contents are poured into 50 ml of water and stirred for 60 seconds, a homogeneous suspension of microcapsules stable up to 2 hours is obtained.

EXAMPLE 7

(A) With a process similar to that disclosed in Example 1, a theophylline granulate with a grain size less than 500 microns was microencapsulated. By applying 6.3% of membrane, microcapsules were obtained which in vitro slowly release theophylline over a time interval of 8 hours.

(B) 125 g of sodium alginate with grain size less than 150 mesh (Tyler) were suspended in 385 ml of a 3% solution of hydroxypropylcellulose in ethyl alcohol. This suspension is added to a counterrotating horizontal blade mixer in which 2500 g of granular sorbitol were placed. Addition is effected in four stages at intervals of 15-20 minutes from each other. After having been dried in a fluidized bed, the product is sifted through an 850 micron sieve.

(C) 800 g of suspending granulate (B) were mixed in a cube mixer for 15 minutes with 40 g of citric acid and 130 g of the orange flavouring used in Example 2. Bags were then prepared using 9.680 g of this mixture and 0.320 g of theophylline microcapsules equivalent to a dosage of 300 mg of theophylline. Contents of a bag were poured into about 100 ml of water and mixed with a teaspoon for 60 seconds. A homogeneous dispersion of the microcapsules is obtained, which is stable for about 2 hours.

EXAMPLE 8

(A) With a process similar to that of Example 1, paracetamol crystals were microencapsulated, with a grain size less than 500 microns, so as to mask its bitter taste. The obtained microcapsules have 4% of ethylcellulose membrane.

(B) 100 g of sodium carrageenan, ground to a grain size smaller than 200 mesh (Tyler), was suspended in 350 g of a 2% solution of polyvinylpyrrolidone in ethyl alcohol in which also 5 g of dioctyl sulphosuccinate were dissolved.

This suspension was added slowly to 2500 g of sucrose crystals placed in a planetary kneader. After drying in a fluidized bed, the product was sifted through an 850 micron sieve.

(C) The granulate was mixed for 15 minutes in a cube mixer with 50 g of raspberry flavouring. Bags containing 9.584 g of this mixture and 0.416 g of paracetamol microcapsules were then prepared, corresponding to a dosage of 400 mg of active substance.

The contents of a bag were poured into 100 ml of water and stirred with a teaspoon for two minutes, obtaining a homogeneous and stable suspension for about one and one-half hours.

It is here to be pointed out that the coating membrane of Example 6, as well as in all of the other Examples of this application, is water-insoluble. In Example 6 the gelatin is crosslinked with glutaric aldehyde, which makes it water-insoluble. In most of the other Examples, the coating membrane used is ethylcellulose, which also is water-insoluble. The membrane applied to the microcapsules in Example 7 was ethylcellulose, the microencapsulation procedure being substantially identical to that disclosed in Example 1.

The following additional disclosure is in full support of the original disclosure and claims as presented in the parent application:

The membrane applied in the microencapsulation process is, as is well known, insoluble both in water and in the gastro-intestinal juices, the microencapsulated drug being released by diffusion through the membrane (for example when the membrane is made of ethylcellulose), or by enzymatic digestion of the membrane (for example when the membrane is made of hardened or cross-linked gelatin), or is insoluble in water and in the gastric juice, but is soluble in the enteric juice of the intestines (this being the case when the membrane is made of gastroresistant polymers such as cellulose acetate phthalate). The polymeric membrane coating is thus insoluble in, but permeable to, both water and the gastro-intestinal juices; or is insoluble both in water and the gastro-intestinal juices, but is destroyed by enzymatic digestion; or is insoluble in water and in the gastric juice, but is soluble in the enteric juices.

A substantial variation in the ratio of the weight of the thickening or suspending agent to the weight of the binder may be employed, e.g., from about 4:1 to about 20:1, preferably from about 5:1 to about 20:1, usually to about 15:1, as shown in the previous Examples and those which follow.

EXAMPLE 9

(A) Preparation of the microcapsules: 600 g of a theophylline granulate having a particle size distribution between 200 and 500 microns was coated with 6.3% by weight of an ethylcellulose-based membrane prepared according to the standard microencapsulation procedure of Example 1 or by coating in a fluid bed coater with 6.3% by weight of an ethylcellulose-based membrane appled by spraying on the theophylline granules a solution of ethylcellulose 5% by weight in ethyl alcohol. This membrane is water-insoluble, but permeable to the gastro-intestinal juices, and the release of the theophylline from the coated granules is thereby sustained over an interval of eight (8) hours.

(B) Preparation of the suspending granulate: 220 g of xanthan gum, having a particle size smaller than 200 mesh (Tyler), was suspended into 560 g of a 10% (w/w) solution of polyvinylpyrrolidone (PVP) in ethylalcohol (the ratio of xanthan gum to PVP being about 4:1). This suspension was sprayed onto 3722 g of sucrose crystals using a fluid bed apparatus. The granulate was finally sieved through an 870 micron sieve.

(C) Preparation of the monodose sachets: 3947.6 g of the suspending granulate (B) were mixed for fifteen (15) minutes in a cube mixer with 320 g of microcapsules (A), 636 g of sucrose, 25 g of apricot flavor, and 11.4 g of talc. This mixture was used to fill monodose sachets having an average weight of 3.295 g.

EXAMPLE 10

(A) Preparation of microcapsules: crystals of potassium chloride were coated on an industrial scale with an ethy-cellulose membrane which is water-insoluble, but permeable both in water and in the gastro-intestinal juices. The coating was prepared following the microencapsulation process described in Example 1.

(B) Preparation of the suspending granulate: 34 kg of xanthan gum, having a particle size less than 200 mesh (Tyler), were suspended in 54 kg of a 10.7% (w/w) solution of polyvinylpyrrolidone (PVP) in ethyl alcohol (the ratio of xanthan gum to PVP being about 5.86:1). This suspension was sprayed onto 265 kg of sucrose crystals placed in a pan coater. The granulate was dried and sieved through an 870 micron sieve.

(C) Preparation of the mixture for single dose bags: 709.3 kg of suspending granulate B) were mixed for sixty (60) minutes, in a cube mixer having a capacity of 1500 liters, with 290.7 kg of potassium chloride microcapsules (A) having a potency of 860 mg/g. This mixture was used for the filling of single dose bags.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. Method of preparing a drug microcapsule formulation consisting essentially of the drug microcapsules and a thickening or suspending agent and a binder and a solid particulate excipient, having the property of being readily dispersible and readily dissolvable in water or aqueous vehicles without clot formation so as to place the drug microcapsules in homogeneous suspension, consisting essentially of the following steps:

(a) providing a thickening or suspending agent having a grain size less than 100 mesh (Tyler) which is insoluble or only slightly soluble in a solvent in which a binder is dissolved in step (b);

(b) suspending the suspending or thickening agent in a dilute organic solvent solution of a solvent-soluble and water-soluble binder; wherein the weight of thickening or suspending agent in relation to the binder is about 4:1 to about 20:1;

(c) coating the suspension around particles of a water-soluble solid sweetener;

(d) drying to evaporate solvent and sieving the obtained product; and (e) mixing the said product with drug microcapsules having a water-insoluble membrane-coating to provide the desired readily-dispersible formulation.

2. Method according to claim 1, wherein the thickening or suspending agent has a grain size lower than 200 mesh (Tyler).

3. Method according to claim 1, wherein the weight of thickening or suspending agent in relation to the binder is about 5:1 to about 20:1.

4. Method according to claim 1, wherein the organic solvent in which the binder is dissolved is a food-grade lower-alkanol.

5. Method according to claim 1, wherein the thickening agent is selected from the group consisting of alginates, carrageenan, agar-agar, gum tragacanth, xanthan gum, guar gum, locust bean gum, karaya gum, modified starch, carboxymethlcellulose, and microcrystalline cellulose, alone or in combination with another hydrocolloid.

6. Method according to claim 5, wherein sodium alginate, sodium carrageenin, or xanthan gum is used as a thickening agent and hydroxypropylcellulose or polyvinylpyrrolidone is used as binder.

7. Method according to claim 1, wherein the water-soluble binder is selected from the group consisting of methylcellulose, hydroxypropylmethylcellulose, hydroxybutylmethylcellulose, hydroxyethylcellulose, hydroxypropylcellulose, polyethyleneglycols, polyvinyl alcohols, and polyvinylpyrrolidone.

8. Method according to claim 1, wherein the inert excipient is selected from the group consisting of sucrose, lactose, levulose, mannitol, dry sorbitol, maltodextrines, glycocoll, alanine, and pentaerythrite.

9. Method according to claim 1, wherein a surfactant is added to the formulation before step (d), for accelerating wettability of the thickening agent.

10. Formulation prepared according to claim 1 in a single-dose bag, for preparing a homogeneous suspension of drug microcapsules, when the bag contents are poured into water or an aqueous base liquid.

11. A dry formulation for preparing a homogeneous suspension of drug microcapsules, when it is poured into water or an aqueous base liquid, consisting essentially of (A) drug microcapsules having a polymeric membrane coating which is permeable by gastrointestinal juices, admixed with (B) coated particles consisting essentially of (a), (b), and (c), (a) being a solvent-soluble and water-soluble binder; and (b) being a thickening or suspending agent having a grain size less than 100 mesh (Tyler) which is insoluble or only slightly soluble in a dilute organic solvent solution in which the binder is soluble; the weight of thickening or suspending agent in relation to the weight of the binder being about 4:1 to about 20:1; a suspension of (a) and (b) being coated around (c), (c) being particles of a water-soluble solid sweetener; the admixture being sieved to a particle size of 870 microns or less.

12. Formulation prepared according to claim 11 in a single-dose bag, for preparing a homogeneous suspension of drug microcapsules, when the bag contents are poured into water or an aqueous base liquid.

13. Formulation according to claim 11, wherein the micro-encapsulated drug is potassium chloride.

14. Method of preparing a drug microcapsule formulation consisting essentially of (A) drug microcapsules having a water-insoluble membrane coating in admixture with (B) coated particles, consisting essentially of (a) a thickening or suspending agent and (b) a binder coated upon (c) a solid particulate excipient, which formulation has the property of being readily dispersible and readily dissolvable in water or aqueous vehicles without clot formation so as to place the drug microcapsules in homogeneous suspension, consisting essentially of the following steps:

(1) providing a thickening or suspending agent (a) having a grain size less than 100 mesh (Tyler) which is insoluble or only slightly soluble in a solvent in which a binder (b) is dissolved in step (2); the thickening or suspending agent (a) being selected from the group consisting of alginates, carrageenan, agar-agar, gum tragacanth, xanthan gum, guar gum, locust bean gum, karaya gum, modified starch, carboxymethylcellulose, and crystalline cellulose, alone or in combination with another hydrocolloid;

(2) suspending the suspending or thickening agent (a) in a dilute organic solvent solution of a solvent-soluble and water-soluble binder (b); the water-soluble binder (b) being selected from the group consisting of methylcellulose, hydroxypropylmethylcellulose, hydroxybutylmethylcellulose, hydroxyethylcellulose, hydroxypropylcellulose, polyethyleneglycols, polyvinyl alcohols, and polyvinylpyrrolidone; the weight of thickening or suspending agent (a) in relation to the binder (b) being about 4:1 to about 20:1;

(3) coating the suspension around particles of a water-soluble solid sweetener (c); the sweetener (c) being selected from the group consisting of sucrose, lactose, levulose, mannitol, dry sorbitol, maltodextrines, glycocoll, alanine, and pentaerythrite;

(4) drying to evaporate solvent and sieving the obtained product (B) to a particle size of 870 microns or less; and (5) mixing the said product (B) with (A) drug microcapsules having a membrane-coating which is water insoluble but permeable by gastrointestinal juices to provide the desired readily-dispersible formulation.

15. Method according to claim 14, wherein the thickening or suspending agent has a grain size less than 200 mesh (Tyler).

16. Method according to claim 15, wherein sodium alginate, sodium carrageenin, or xanthan gum is used as thickening agent and hydroxypropylcellulose or polyvinylpyrrolidone is used as binder.

17. Method according to claim 16, wherein the weight of thickening or suspending agent in relation to the binder is about 5:1 to about 20:1.

18. Method according to claim 17, wherein a surfactant is added to the formulation before step (4) for accelerating wettability of the thickening agent.

19. Method according to claim 14, wherein the organic solvent in which the binder is dissolved is a food-grade lower-alkanol.

20. A dry formulation for preparing a homogeneous suspension of drug microcapsules, when it is poured into water or an aqueous base liquid, consisting essentially of (A) drug microcapsules having a polymeric membrane coating which is water-insoluble but permeable by gastrointestinal juices, admixed with (B) coated particles consisting essentially of (a), (b), and (c), (a) being a solvent-soluble and water-soluble binder; and (b) being a thickening or suspending agent having a grain size less than 100 mesh (Tyler) which is insoluble or only slightly soluble in a dilute organic solvent solution in which the binder is soluble; the weight of thickening or suspending agent in relation to the weight of the binder being about 4:1 to about 20:1; a suspension of (a) and (b) being coated around (c), (c) being particles of a water-soluble solid sweetener; the thickening agent (a) being selected from the group consisting of alginates, carrageenan, agar-agar, gum tragacanth, xanthan gum, guar gum, locust bean gum, karaya gum, modified starch, carboxymethylcellulose, and crystalline cellulose, alone or in combination with another hydrocolloid; the water-soluble binder (b) being selected from the group consisting of methylcellulose, hydroxypropylmethylcellulose, hydroxybutylmethylcellulose, hydroxyethylcellulose, hydroxypropylcellulose, polyethyleneglycols, polyvinyl alcohols, and polyvinylpyrrolidone; the sweetener (c) being selected from the group consisting of sucrose, lactose, levulose, mannitol, dry sorbitol, maltodextrines, glycocoll, alanine, and pentaerythrite; and the admixture having a particle size of 870 microns or less.

21. Formulation according to claim 20, wherein the microencapsulated drug is potassium chloride.

22. Formulation according to claim 20, wherein sodium alginate, sodium carrageenin, or xanthan gum is used as a thickening agent and hydroxypropyl cellulose or polyvinylpyrrolidone is used as binder.

* * * * *

UNITED STATES PATENT AND TRADEMARK OFFICE
CERTIFICATE OF CORRECTION

PATENT NO. : 5,008,117
DATED : Apr. 16, 1991
INVENTOR(S) : Massimo Calanchi, Leonardo Gentilini, Marco Marconi It is certified that error appears in the above-identified patent and that said Letters Patent is hereby corrected as shown below:

Title Page, [57], ABSTRACT, 6th line; "extermoraneous" should read -- extemporaneous --.
Column 3, last line; "alcohols, polyvinylpyrrolidone" should read -- alcohols, and polyvinylpyrrolidone --. (PA 12-7-88, P. 4)
Column 4, line 4; "cited;" should read -- cited: --. (PA 12-7-88, P. 5)
Column 5, line 11; "10.5 of" should read -- 10.5 g of --.
Column 9, line 24; "carboxymethlcellulose," should read -- carboxymethylcellulose -- .
Column 9, line 65; "11" should read -- 1 --. (R&A 7-17-90, P.6, formerly Claim 23)

Signed and Sealed this

Twenty-ninth Day of September, 1992

Attest:

DOUGLAS B. COMER

*Attesting Officer*     *Acting Commissioner of Patents and Trademarks*